(12) United States Patent
Chuang et al.

(10) Patent No.: US 12,054,740 B2
(45) Date of Patent: Aug. 6, 2024

(54) METHOD FOR INHIBITING GROWTH OF CANCER CELLS USING ANTI-CANCER COMPOSITION WITH MESENCHYMAL STEM CELLS CONDITIONED MEDIUM

(71) Applicant: GROWGENE BIOTECH INC., Taipei (TW)

(72) Inventors: Pei-Chuan Chuang, Taipei (TW); Chin-Jing Huang, Taipei (TW)

(73) Assignee: Growgene Biotech, Inc., Taipei (TW)

(*) Notice: Subject to any disclaimer, the term of this patent is extended or adjusted under 35 U.S.C. 154(b) by 0 days.

(21) Appl. No.: 17/686,811

(22) Filed: Mar. 4, 2022

(65) Prior Publication Data
US 2023/0116104 A1    Apr. 13, 2023

(30) Foreign Application Priority Data

Oct. 13, 2021    (TW) .................................. 110137987

(51) Int. Cl.
| | | |
|---|---|---|
| A61K 35/28 | (2015.01) | |
| A61K 38/18 | (2006.01) | |
| A61K 38/21 | (2006.01) | |
| C12N 5/073 | (2010.01) | |
| C12N 5/0775 | (2010.01) | |

(52) U.S. Cl.
CPC ........ *C12N 5/0605* (2013.01); *C12N 2500/02* (2013.01); *C12N 2501/115* (2013.01); *C12N 2501/155* (2013.01); *C12N 2501/2318* (2013.01); *C12N 2501/24* (2013.01); *C12N 2501/25* (2013.01); *C12N 2501/415* (2013.01)

(58) Field of Classification Search
CPC ............. C12N 5/0605; C12N 2500/02; C12N 2501/115; C12N 2501/155; C12N 2501/2318; C12N 2501/24; C12N 2501/25; C12N 2501/415
See application file for complete search history.

(56) References Cited

U.S. PATENT DOCUMENTS

| | | | | |
|---|---|---|---|---|
| 9,308,238 | B2 * | 4/2016 | Scheel ..................... | A61P 35/00 |
| 9,943,545 | B2 * | 4/2018 | Rezner .................... | A61P 35/02 |
| 2004/0126361 | A1 * | 7/2004 | Saifer ..................... | A61K 38/215 |
| | | | | 424/85.6 |
| 2018/0333491 | A1 * | 11/2018 | Shen ....................... | A61P 35/00 |

FOREIGN PATENT DOCUMENTS

WO    WO-2021194906 A1 *  9/2021

OTHER PUBLICATIONS

Kumar, P. L., et al., "The mesenchymal stem cell secretome: A new paradigm towards cell-free therapeutic mode in regenerative medicine," Cytokine & Growth Factor Reviews 46: 1-9. doi: 10.1016/j.cytogfr.2019.04.002. Epub Apr. 2, 2019. (Year: 2019).*

Gauthaman, K., et al., "Human umbilical cord Wharton's jelly stem cell (hWJSC) extracts inhibit cancer cell growth in vitro," Journal of Cellular Biochemistry 113(6): 2027-2039. doi: 10.1002/jcb.24073. (Year: 2012).*

Shen, C., et al., "Human umbilical cord matrix-derived stem cells expressing interferon-β gene inhibit breast cancer cells via apoptosis," Oncotarget 7(23): 34172-34179. doi: 10.18632/oncotarget.8997. Jun. 7, 2016. (Year: 2016).*

Ma, S., et al., "Human umbilical cord mesenchymal stem cells inhibit C6 glioma growth via secretion of dickkopf-1 (DKK1)," Mol Cell Biochem 385(1-2): 277-286. doi: 10.1007/s11010-013-1836-y. Epub Oct. 9, 2013. (Year: 2013).*

Moniri, M. R., et al., "TRAIL-engineered pancreas-derived mesenchymal stem cells: characterization and cytotoxic effects on pancreatic cancer cells," Cancer Gene Therapy 19(9): 652-658. doi: 10.1038/cgt.2012.46. Epub Jul. 6, 2012. (Year: 2012).*

Choi, Y. U., et al., "TRAIL-overexpressing Adipose Tissue-derived Mesenchymal Stem Cells Efficiently Inhibit Tumor Growth in an H460 Xenograft Model," Cancer Genomics & Proteomics 18(4): 569-578. doi: 10.21873/cgp.20281. Jul. 2021 (Year: 2021).*

Pereira, T., et al., "Effects of Human Mesenchymal Stem Cells Isolated from Wharton's Jelly of the Umbilical Cord and Conditioned Media on Skeletal Muscle Regeneration Using a Myectomy Model," Stem Cells International 2014:376918. doi: 10.1155/2014/376918. Epub Oct. 14, 2014. (Year: 2014).*

Alessio, N., et al., "The secretome of MUSE cells contains factors that may play a role in regulation of stemness, apoptosis and immunomodulation," Cell Cycle 16(1): 33-44. doi: 10.1080/15384101.2016.1211215. Epub Jul. 27, 2016 (Year: 2016).*

Daneshmandi, L., et al., "Emergence of the Stem Cell Secretome in Regenerative Engineering," Trends in Biotechnology 38(12): 1373-1384. doi: 10.1016/j.tibtech.2020.04.013. Epub Jul. 1, 2020. (Year: 2020).*

Sipos, F., and Muzes, G., "Disagreements in the therapeutic use of mesenchymal stem cell-derived secretome," World Journal of Stem Cells 14(6): 365-371. doi: 10.4252/wjsc.v14.6.365. Jun. 26, 2022. (Year: 2022).*

Bartosh, T. J., et al., "Aggregation of human mesenchymal stromal cells (MSCs) into 3D spheroids enhances their antiinflammatory properties," Proceedings of the National Academy of Sciences U.S.A. 107(31):13724-9. doi: 10.1073/pnas.1008117107. Aug. 3, 2010 (Year: 2010).*

(Continued)

*Primary Examiner* — Tracy Vivlemore
*Assistant Examiner* — Eric J Rogers
(74) *Attorney, Agent, or Firm* — Rosenberg, Klein & Lee

(57) ABSTRACT

The invention discloses a method for inhibiting the growth of cancer cells by use of an anti-cancer composition containing a conditioned cell culture medium from mesenchymal stem cells and cytokines. It comprises the steps of applying a composition with a conditioned cell culture medium from stem cells and at least one cytokine to cancer cells for growth inhibition of the cancer cells. The cell culture medium can be conditioned with Wharton's Jelly mesenchymal stem cells (WJMSCs) as an WJMSCs-conditioned cell culture medium, and the at least one cytokine is selected from a group consisting of bone morphogenetic protein-4, Dickkopf-related protein, Interferon-β and tumor necrosis factor-related apoptosis-inducing ligand.

3 Claims, 7 Drawing Sheets

(56) References Cited

OTHER PUBLICATIONS

Tanaka, T., et al., "IL-6 in inflammation, immunity, and disease," Cold Spring Harbor Persectives in Biology 6(10): a016295. doi: 10.1101/cshperspect.a016295. (Year: 2014).*
Montgomery, D. C., "Design and Analysis of Experiments," Eighth Edition. Arizona State University. Copyright 2013. (Year: 2013).*

* cited by examiner

METHOD FOR INHIBITING GROWTH OF CANCER CELLS USING ANTI-CANCER COMPOSITION WITH MESENCHYMAL STEM CELLS CONDITIONED MEDIUM

BACKGROUND OF THE INVENTION

1. Field of the Invention

The present invention discloses a method for inhibiting the growth of cancer cells by use of an anti-cancer composition with a conditioned cell culture medium from mesenchymal stem cells and cytokines.

2. Description of Related Art

Cancer is a disease in which cells are abnormally proliferation so as to affect normal physiological functions of living organisms. The conventional therapeutic methods for cancers include surgical removal of abnormally growing cells and tissues, radiation or drug therapies to inhibit growth and to induce cell death of the cancer cells. However, the conventional therapeutic methods also affect the growth of human normal cells and even induce cell death of the normal cells. So the conventional therapeutic methods affect normal physiological functions of the patients and might make the patients weaker.

Currently, in treatment of cancers, there are many different types of targeted drugs developed for targeting specific differences that a cancer cell has, but not every cancer has a corresponding target drug. In addition, patients with cancers usually cannot afford any expensive target drugs. Therefore, it is important to develop a therapeutic method which can be applied to multiple cancers and is specific to the cancer cells.

SUMMARY OF THE INVENTION

The present invention discloses a method for inhibiting the growth of cancer cells by use of an anti-cancer composition containing a conditioned cell culture medium from stem cells and cytokines. It comprises steps of preparing a conditioned cell medium from stem cells and at least one cytokine for obtainment of an anti-cancer composition and applying the anti-cancer composition to cancer cells.

In an embodiment of the present invention, the cell culture medium is conditioned with Wharton's Jelly mesenchymal stem cells (WJMSCs), and a preparation method of the conditioned cell culture medium from WJMSCs comprises the steps of incubating the WJMSCs in a medium for 3 to 5 days, collecting and sterilizing the medium to obtain the conditioned medium from WJMSCs.

In an embodiment of the present invention, at least one cytokine is selected from the group consisting of bone morphogenetic protein-4 (BMP-4), Dickkopf-related protein (Dkk), Interferon-β (IFN-β), and tumor necrosis factor-related apoptosis-inducing ligand (TRAIL).

In an embodiment of the present invention, a concentration of the BMP-4 ranges from 10 to 1000 ng/mL, a concentration of the Dkk ranges from 10 to 1000 ng/mL, a concentration of the IFN-β ranges from 1 to 100 pg/mL, and a concentration of the TRAIL ranges from 1 to 100 ng/mL.

In an embodiment of the present invention the concentration of the BMP-4 is 50 ng/mL, the concentration of the Dkk is 10 ng/mL, the concentration of the IFN-β is 10 pg/mL, and the concentration of the TRAIL is 1 ng/mL.

In an embodiment of the present invention, the cancer cells are human melanoma cells or breast cancer cells.

In an embodiment of the present invention, the breast cancer cells are ductal carcinoma cells.

Accordingly, the present invention applies a composition with a conditioned medium from stem cells and cytokines to cancer cells, in order for inhibiting the growth of the cancer cells effectively. In addition, it has extremely high safety that the cytokines used in the present invention do not affect the growth of normal cells.

DETAILED DESCRIPTION OF THE PREFERRED EMBODIMENT

Figure 1:
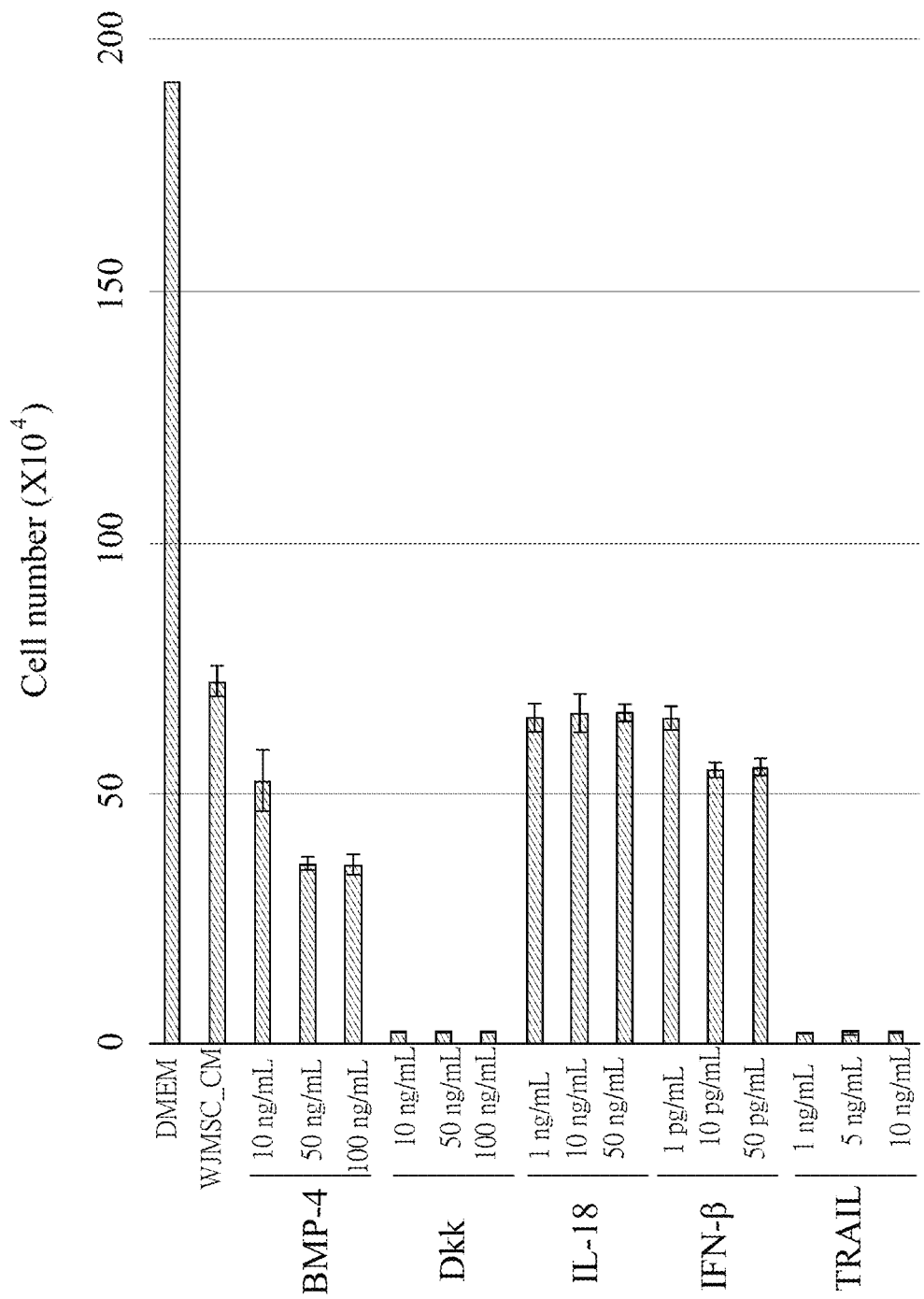
FIG. 1 is a bar chart showing effects of different cytokines on the growth of A375 cells.

In order to provide a thorough understanding of the present invention, the advantages and the scope of the present invention are disclosed in the following embodiments with reference to the accompanying figures, but the description of the embodiments is not intended as a limitation to the scope of the present invention.

I. Preparation of Conditioned Cell Culture Medium from Wharton's Jelly Mesenchymal Stem Cells Wharton's Jelly mesenchymal stem cells (WJMSCs) used in the present invention is obtained from Bioresource Collection and Research Center (BCRC) of Food Industry Research and Development Institute and has an accession number of RM60596. WJMSCs are incubated in an α-MEM complete medium at 37° C. in an incubator supplemented with 5% carbon dioxide ($CO_2$). The α-MEM complete medium contains 20% fetal bovine serum (FBS) and 4 ng/mL basic fibroblast growth factor (bFGF).

To prepare the conditioned cell culture medium, $2 \times 10^5$ cells of WJMSCs were seeded into a 75 $cm^2$ flask and 10 mL of the α-MEM complete medium was added into the flask. The WJMSCs was then incubated at 37° C. in an incubator supplemented with 5% $CO_2$ for 3 to 4 days. The cell culture medium was collected and centrifuged at 4° C. and 2000 rpm for 10 minutes, and the supernatant was collected. The supernatant was then filtered by a 0.22 nm filter to remove impurities in the supernatant. The filtrate obtained is referred to the conditioned cell culture medium derived from WJMSCs is abbreviated as WJMSC-CM hereafter. The WJMSC-CM was aliquoted and stored at 4° C. The WJMSC-CM was used within 2 days after collection, and the WJMSM-CM more than 2 days after collection will be discarded.

II. Effect of Cytokines and WJMSC-CM on Cell Growth (1) Optimal Concentration of Cytokines Human melanoma cell line A375 and human breast ductal carcinoma cell line MCF-7 are used in this experiment. Both the A375 cell line and the MCF-7 cell line are purchased from BCRC of Food Industry Research and Development Institute. The accession number of the A375 cell line is BCRC60039 and the accession number if the MCF-7 cell line is BCRC60436. The experimental procedure is briefly described as follows: A375 cells and of MCF-7 cells were respectively seeded into a 6-well plate at $1\times10^4$ cells/well and $2\times10^4$ cells/well. The cell culture medium for the two cell lines is a complete DMEM medium which contains 10% FBS and high glucose content. At the next day, the cell culture medium was removed and the cells were washed by a PBS buffer twice. The cells were then incubated with 2 mL of fresh complete DMEM medium, 2 mL WJMSC-CM prepared by the abovementioned method, or 2 mL cytokine-containing WJMSC-CM. The cell number of the A375 cell line was counted after incubation for 8 days, and the cell number of the MCH-7 cell line was counted after incubation for 10 days.

The cytokines used in the experiment comprises bone morphogenetic protein-4 (BMP-4), Dickkopf-related protein (Dkk), Interleukin-18 (IL-18), Interferon-β (IFN-β), and tumor necrosis factor-related apoptosis-inducing ligand (TRAIL). In the following test, the concentration used of BMP-4 is 10, 50, or 100 ng/mL, the concentration used of Dkk is 10, 50, or 100 ng/mL, the concentration used of IL-18 is 1, 10, or 50 ng/mL, the concentration used of IFN-β is 1, 10, or 50 pg/mL, and the concentration used of TRAIL is 1, 5, or 10 ng/mL.

FIG. 1 shows cell number of A375 cells after co-incubation with cytokines. The "DMEM" group is a negative control group in which the cells were incubated with the DMEM complete medium without any cytokines. The cells incubated with WJMSC-CM without any cytokines are referred to as "WJMSC CM" group, which is also a negative control group. Compared to the DMEM group, cell number of the WJMSC_CM group is significantly decreased. Further, cell number of the cells of the groups treated with different cytokines are also decreased significantly compared to the DMEM groups. In the BMP-4 group, there is little difference between the cell number of the cells treated with 50 ng/mL BMP-4 and 100 ng/mL BMP-4, so the cells will be treated with of 50 ng/mL BMP-4 in the subsequent experiment. In the IL-18 group, there is little difference between the cell number of cells treated with three concentrations of IL-18 and the cell number of the WJMSC_CM group, and there is no statistical difference between the IL-18 groups and the WJMSC_CM group. Therefore, IL-18 will not be used in the subsequent experiment. In the Dkk group, there is little different between the cell number of cells treated with three concentrations of with Dkk, so the cells will be treated with 10 ng/mL Dkk in the subsequent experiment. In the IFN-β group, there is little difference between the cells treated with 10 pg/mL IFN-β and 50 pg/mL IFN-β, so the cells will be treated with 10 pg/mL IFN-β in the subsequent experiment. And in the TRAIL group, there is little difference between the cell number of cells treated with three concentrations of TRAIL, so the cells will be treated with 1 ng/mL TRAIL in the subsequent experiment.

Figure 2:
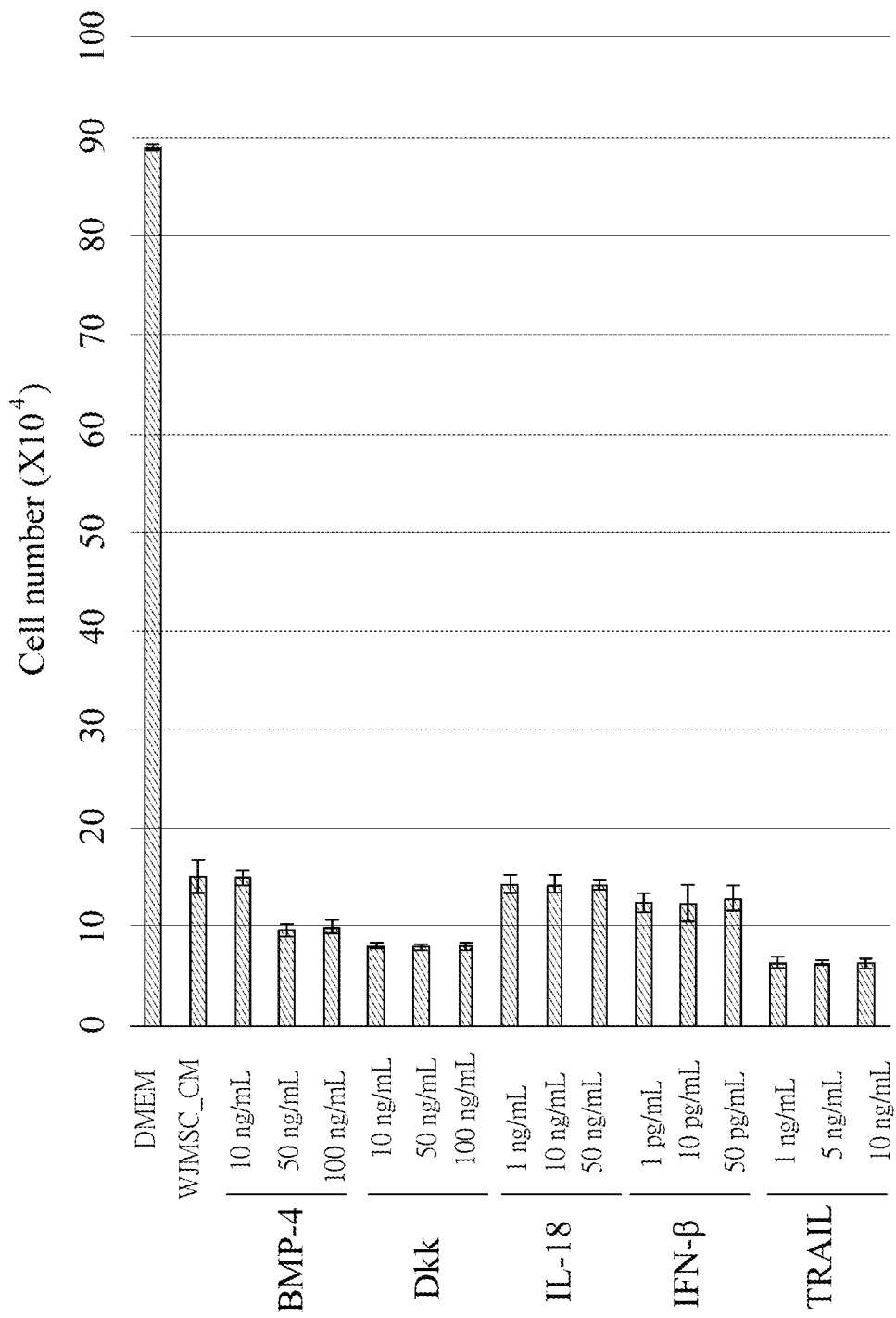
FIG. 2 is a bar chart showing effects of different cytokines on the growth of MCF-7 cells.

FIG. 2 shows cell number of MCF-7 cells after co-incubation with cytokines. The "DMEM" group is a negative control group in which the cells were incubated with the DMEM complete medium without any cytokines. The cells incubated with WJMSC-CM without any cytokines are referred to as "WJMSC_CM" group, which is also a negative control group. Compared to the "DMEM" group, cell number of MCF-7 cells in the "WJMSC_CM" group is significantly decreased. Further, cell number of MCF-7 cells of the groups treated with different cytokines are also decreased significantly compared to the "DMEM" group. In the "BMP-4" group, there is little difference between the cell number of the cells treated with 50 ng/mL BMP-4 and 100 ng/mL BMP-4, so the cells will be treated with of 50 ng/mL BMP-4 in the subsequent experiment. In the "IL-18" group, there is little difference between the cell number of cells treated with three concentrations of IL-18 and the "WJMSC_CM" group, and there is no statistical difference between the "IL-18" groups and the "WJMSC_CM" group. Therefore, IL-18 will not be used in the subsequent experiment. In the "Dick" group, there is little different between the cell numbers of cells treated three concentrations of with Dick, so the cells will be treated with of 10 ng/mL Dkk in the subsequent experiment. In the "IFN-β" group, there is little difference between the cells treated with 10 pg/mL IFN-β and 50 pg/mL ITN-β, so the cells will be treated with 10 pg/mL IFN-(3 in the subsequent experiment. And in the "TRAIL" group, there is little difference between the cell number of cells treated with three concentrations of TRAIL, so the cells will be treated with 1 ng/mL TRAIL in the subsequent experiment.

(2) Effect of WJMSC-CM Accompanying with Cytokines on Cell Growth

WJMSCs, A375 cells and MCF-7 cells were respectively seeded into a 6-well culture plate at $1\times10^4$ cells/well, $1\times10^4$ cells/well and $1\times10^5$ cells/well. The cell culture medium used for WJMSCs is the α-MEM complete medium, and the cell culture medium used for A375 cells and MCF-7 cells is the DMEM complete medium. All the three cell lines were incubated at 37° C. in an incubator supplemented with 5% $CO_2$. The cell culture medium was removed at the next day, and the cells were incubated with fresh medium containing different kinds of cytokines. After 5-day incubation, the number of the cells was counted to evaluate cell growth. The WJMSCs is used as a negative control.

Figure 3:
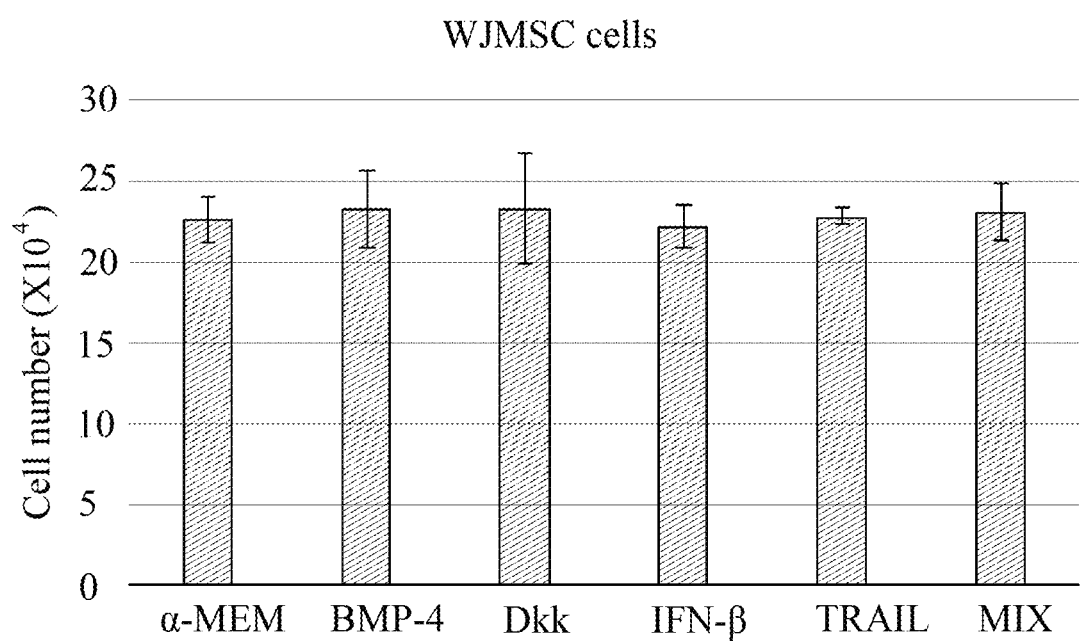
FIG. 3 is a bar chart showing effects of different cytokines on the growth of WJMSCs.

FIG. 3 shows cell number of WJMSCs after treating with different cytokines. Cells in the "α-MEM" group were not treated with any cytokine. The cytokines used in this experiment comprises BMP-4 Dkk, IFN-β and TRAIL. Cells in the "mixture" group were simultaneously treated with the abovementioned four cytokines. In this experiment, the concentration of BMP-4 is 50 ng/mL, the concentration of Dkk is 10 ng/mL, the concentration of IFN-β is 10 pg/mL, and the concentration of TRAIL is 1 ng/mL. According to FIG. 3, the four cytokines do not affect the growth of WJMSCs either treated alone or simultaneously.

In the following experiment, the "DMEM" group and the "α-MEM" group refer to cells respectively incubated with the DMED complete medium and the α-MEM complete medium without any cytokines and are refer to as negative control. The "WJMSC_CM" group refers to cells incubated with WJMSC-CM without any cytokines. The "mixture" group refers to cells incubated with the α-MEM complete medium or the DMEM complete medium containing BMP-4, Dick, IFN-β, and TRAIL. The "mixture/WJMSC_CM" group refers cell to cells incubated with WJMSC-CM containing BMP-4, Dkk, IFN-β, and TRAIL.

Figure 4:
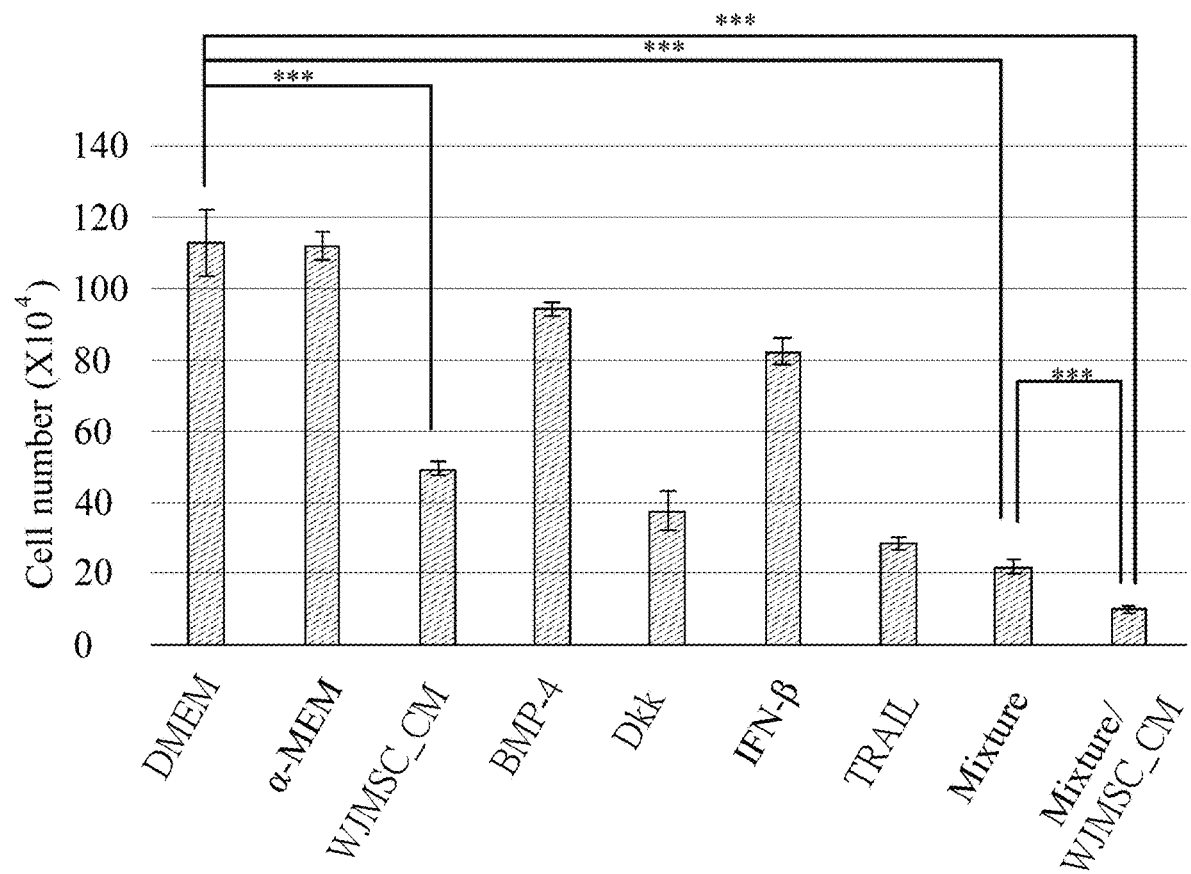
FIG. 4 is a bar chart showing effects of cytokines in company with a conditioned medium from stem cells on the growth of A375 cells.
Figure 5:
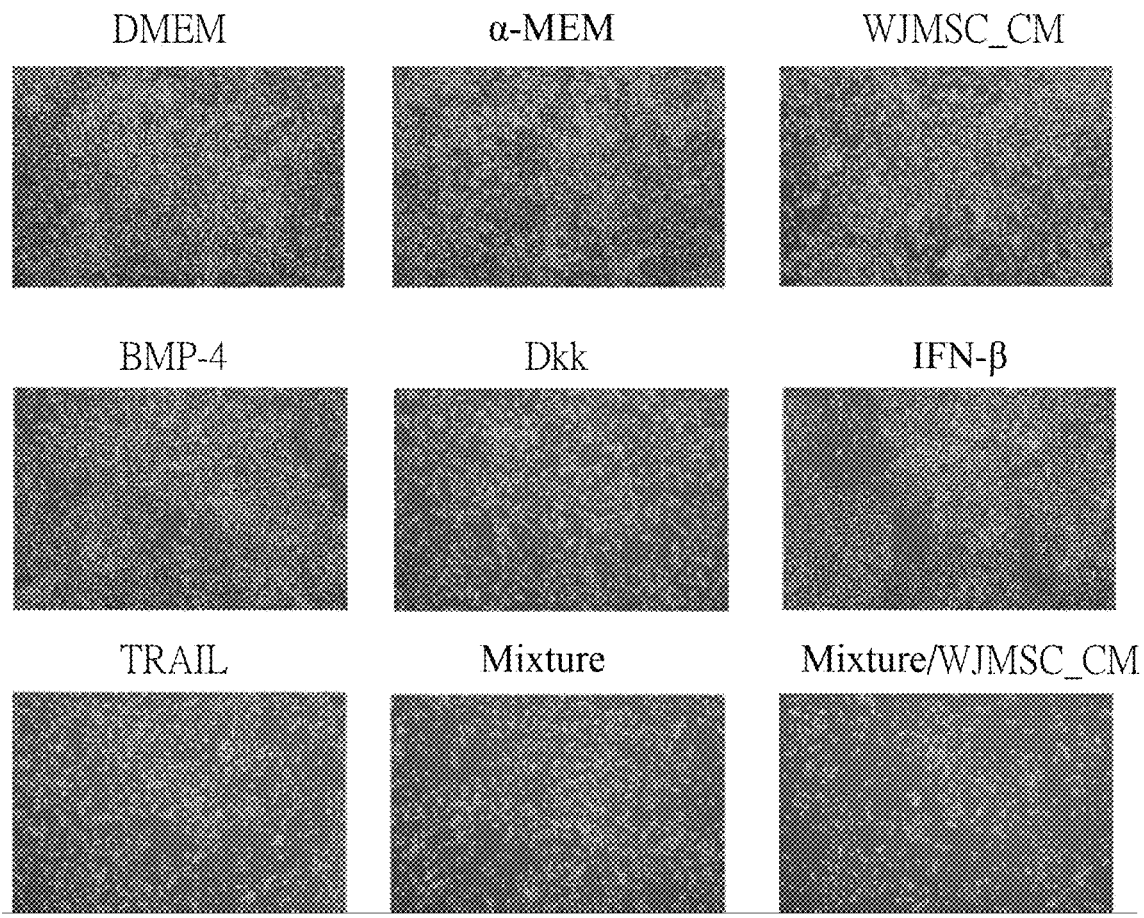
FIG. 5 is a microscopic photograph showing effects of cytokines in company with a conditioned medium from stem cells on the growth of A375 cells.

FIG. 4 shows experimental result of A375 cells. Compare to the two control groups, cell number of the "WJMSC_CM" group is significantly decreased (p<0.001). The cell number of the "mixture" group is also significantly decreased compared to the control groups (p<0.001). In addition, the cell number of the "mixture/WJMSC_CM" group is significantly decreased compared to the "mixture" group (p<0.001). This result indicates that WJMSC-CM accompanying with the four cytokines inhibit the growth of A375 cells more effectively. FIG. 5 shows microscopic photographs of A375 cells in which the cell number of the "mixture/WJMSC_CM" group is significantly less than that of the other groups.

Figure 6:
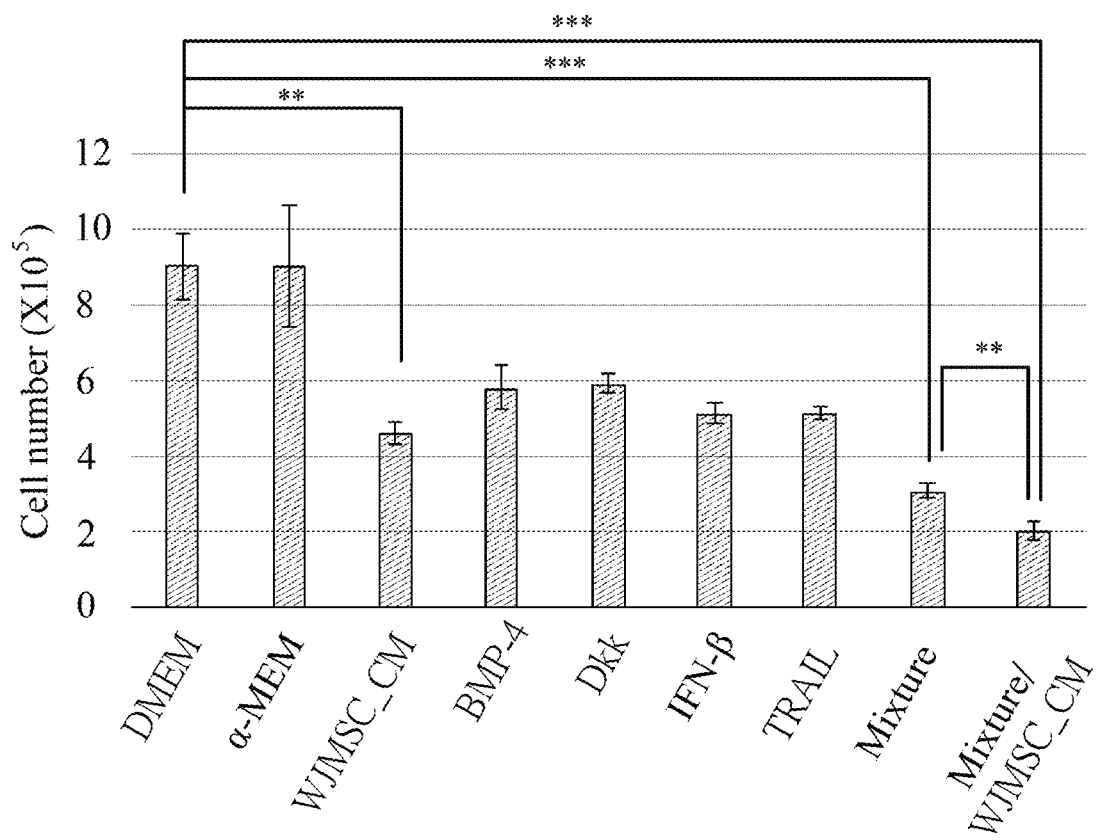
FIG. 6 is a bar chart showing effects of cytokines in company with a conditioned medium from stem cells on the growth of MCF-7 cells.
Figure 7:
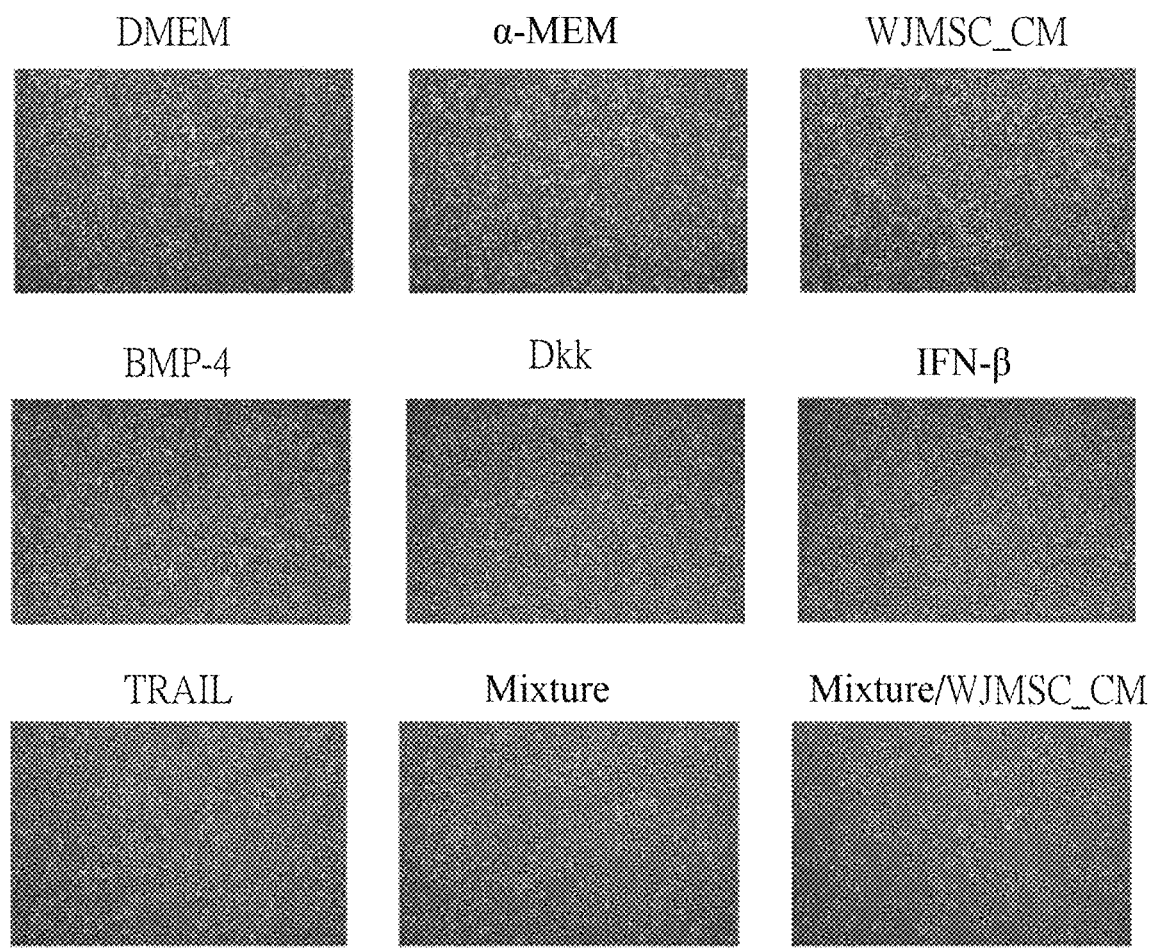
FIG. 7 is a microscopic photograph showing effects of cytokines in company with conditioned medium from stem cells on the growth of MCF-7 cells.

FIG. 6 shows experimental result of MCF-7 cells. Compare to the two control groups, cell number of the "WJMSC_CM" group is significantly decreased (p<0.01). The cell number of the "mixture" group is also significantly decreased compared to the control groups (p<0.001). In addition, the cell number of the "mixture/WJMSC_CM" group is significantly decreased compared to the "mixture" group (p<0.01). This result indicates that WJMSC-CM accompanying with the four cytokines inhibit the growth of MCF-7 cells more effectively. FIG. 7 shows microscopic photographs of MCF-7 cells in which the cell number of the mixed/WJMSC_CM group is significantly less than that of the other groups.

Accordingly, in the method for inhibiting the growth of cancer cells by use of a composition with a conditioned cell culture medium derived from stem cells and at least one cytokine of the present invention, the growth of cancer cells was inhibited effectively by using a conditioned cell culture medium derived from WJMSCs accompanying with cytokines. The cytokines, which used in the present invention do not affect the growth of normal cells, have high safety to use.

What is claimed is:

1. A method for in vitro inhibiting growth of cancer cells by an anti-cancer composition, comprising:
   A. preparing a conditioned cell culture medium from Wharton's Jelly mesenchymal stem cells (WJMSCs) and adding a cytokine mixture into the conditioned cell culture medium for obtainment of the anti-cancer composition; and
   B. applying the anti-cancer composition to cancer cells;
   wherein the cytokine mixture consists of a combination of a bone morphogenetic protein-4, Dickkopf-related protein, Interferon-β and tumor necrosis factor-related apoptosis-inducing ligand;
   wherein a concentration of the bone morphogenetic protein-4 ranges from 10 to 1000 ng/mL, a concentration of the Dickkopf-related protein ranges from 10 to 1000 ng/mL, a concentration of the Interferon-β ranges from 1 to 100 pg/mL, and a concentration of the tumor necrosis factor-related apoptosis-inducing ligand ranges from 1 to 100 ng/mL in the anti-cancer composition, and
   wherein the cancer cells are human melanoma cells.

2. The method as claimed in claim 1, wherein the step A for preparation of the conditioned cell culture medium from WJMSCs further comprises the steps of incubating WJMSCs in an a-MEM medium containing 20% fetal bovine serum (FBS) and 4 ng/mL basic fibroblast growth factor (bFGF) for 3 to 5 days, and collecting and sterilizing the a-MEM medium to obtain a WJMSCs-conditioned cell culture medium.

3. The method as claimed in claim 1, wherein the concentration of the bone morphogenetic protein-4 is 50 ng/mL in the anti-cancer composition, the concentration of the Dickkopf-related protein is 10 ng/mL in the anti-cancer composition, the concentration of the Interferon-β is 10 pg/mL in the anti-cancer composition, and the concentration of the tumor necrosis factor-related apoptosis-inducing ligand is 1 ng/mL in the anti-cancer composition.

* * * * *